Figure 1A:

United States Patent [19]

Kuri-Harcuch et al.

[11] Patent Number: 5,030,105
[45] Date of Patent: Jul. 9, 1991

[54] PROCESS FOR THE LONG-TERM SURVIVING CULTURE OF HEPATOCYTES

[75] Inventors: Walid Kuri-Harcuch; Tomas Mendoza-Figueroa, both of México D. F., Mexico

[73] Assignee: Centro de Investigacion y Estudios Avanzados del Instituto Politecnico Nacional, Apartado Postal, Mexico

[21] Appl. No.: 436,600

[22] Filed: Nov. 15, 1989

Related U.S. Application Data

[62] Division of Ser. No. 741,850, Jun. 6, 1985, Pat. No. 4,914,032.

[51] Int. Cl.$^5$ .............. C12Q 1/02; C12Q 1/00; C12N 5/00
[52] U.S. Cl. .......................... 435/29; 435/4; 435/240.1; 435/240.243; 435/240.31
[58] Field of Search ........... 435/4, 29, 240.1, 240.243, 435/240.31, 948

[56] References Cited

PUBLICATIONS

Althaus, "Depatocyte Cultures as a Research Tool in Pharmacology and Toxicology", Vet. Pharm. Toxicol., pp. 465–478, 1983.
J. of Toxicological and Environmental Health, 26, 293–308 (1989).
Toxicology, 52, 273–286 (1988).

*Primary Examiner*—Elizabeth C. Weimar
*Assistant Examiner*—Gail Poulos
*Attorney, Agent, or Firm*—Abelman Frayne Rezac & Schwab

[57] ABSTRACT

A process is disclosed for the long term surviving culture of hepatocytes maintaining their morphological and functional characteristics for long-term-periods, suitable to assest the acute and chronic hepatotoxicity of drugs, chemicals and environmental pollutants. The long term surviving culture of hepatocytes is carried out in a culture media containing fibroblast cells or fibroblast cell products treated to prevent cell multiplication and inoculated under controlled density.

2 Claims, 4 Drawing Sheets

FIG.4a
FIG.4b
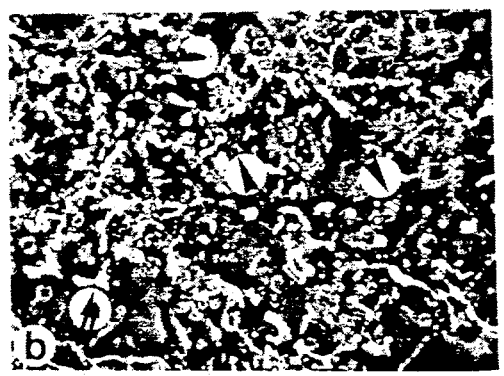
FIG.4c
FIG.4d
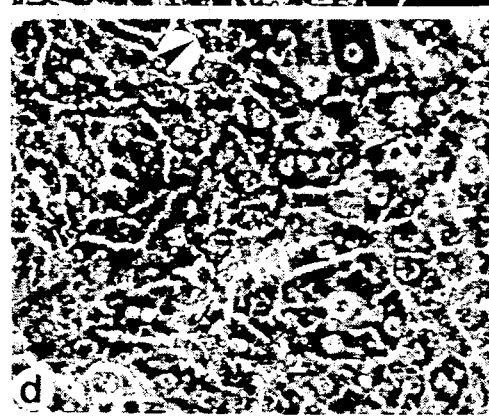
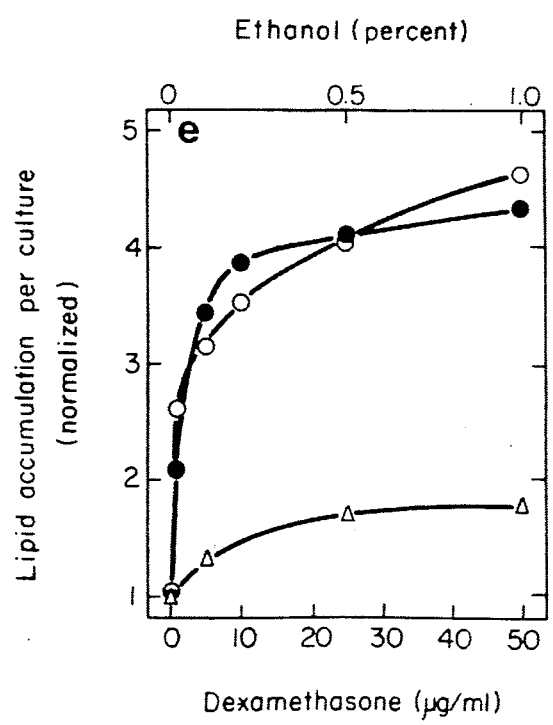
FIG.4e

PROCESS FOR THE LONG-TERM SURVIVING CULTURE OF HEPATOCYTES

This application is a division of application Ser. No. 741,850, now U.S. Pat. No. 4,914,032, filed Jun. 6, 1985.

FIELD OF THE INVENTION

The process relates to the preparation of hepatocyte cultures for maintaining morphological and functional characteristics suitable to test acute and chronic hepatotoxicity of drugs, chemicals and environmental pollutants.

This invention is in the field of biology, in particular cell biology, with important applications to the pharmaceutical and toxicological sciences.

BACKGROUND OF THE INVENTION

The most common methods for in Vitro cultivation of adult hepatocytes do not allow long-term survival neither expression of their differentiated functions. In well known methods, hepatocytes can be cultivated in tissue culture dishes for only 3-8 days after which they do not show characteristic morphology neither express their differentiated functions. (For references see G. Michalopoulos and H. C. Pitot, Exptl. Cell Res., 94, 70, 1975).

Attempts have been made to extend the survival of the cultivated hepatocytes by improving both the culture medium (G. M. Williams, E. Bermudez, R. H. C. San, P. J. Goldblatt, and M. F. Laspia, In Vitro, 14, 824, 1978; P. E. Schwarse, A. E. Solheim, and P. O. Seglen, In Vitro, 18, 43, 1982) and the substratum of the culture dishes to which liver cells have to attach. Hepatocytes have been cultivated on collagen coated dishes and collagen membranes (G. Michalopoulos, and H. C. Pitot, Exptl. Cell Res., 94, 70, 1975), nitrocellulose filters (C. R. Savage, and R. J. Bonney, Exptl. Cell Res., 114, 307, 1978), collagen gel-coated nylon meshes (A. E. Sirica, W. Richards, Y. T. Sukada, C. A. Sattler, and H. C. Pitot, Proc. Natl. Acad. Sci, USA, 76, 283, 1979), fibronectin coated dishes (J. Deschenes, J. P. Valet, and N. Marceau, In Vitro, 16, 722, 1980), dishes with extracellular matrix produced by bovine corneal endothelial cells (C. Guguen-Guillouzo, D. Seignoux, Y. Courtois, P. Brissot, N. Marceau, D. Glaise, and A. Guillouzo, Biol, Cell., 46, 11, 1982), or with connective tissue biomatrix obtained from liver (M. Rojkind, Z. Gatmaitan, S. Mackensen, M. A. Giambrone, P. Ponce, and L. Reid, J. Cell Biol., 87, 225, 1980). Although epithelial morphology and some differentiated functions are conserved for longer periods, changes in genetic expression occur in some cases leading to foetal-like phenotype.

Another useful approach for cultivating epithelial cells is their coculture with feeder cells; these feeder cells are x-irradiated being unable themseleves to multiply, but they exhibit active metabolism (T. T. Puck, P. I. Marcus and S. J. Cieciura, J. Exp. Med., 103, 273, 1956). Incubation of feeder cells with mitomycin-C gives the same results (I. MacPherson and A. Bryden, Exp. cell Res. 69, 240, 1971; J. Taylor Papadimitriou, M. Shearer and M. G. P. Stocker, Int. J. Cancer, 20, 903, 1977; J. G. Rheinwald, Meth. Cell Biol., 21, 229, 1980). Epithelial cells have been therefore cocultured with feeder cells, like 3T3 murine fibroblasts (J. G. Rheinwald and H. Green Cell, 6, 331, 1975) or other types of murine 3T6 or human fibroblasts (J. Taylor-Papadimitriou, M. Shearer, and M. G. P. Stocker, Int. J. Cancer, 20, 903, 1977; R. C. Armstrong and W. Rosenau, Cancer Res., 38, 894, 1978; A. L. Epstein, and H. S., Kaplan, Cancer Res. 39, 1748, 1979).

However, hepatocyte coculture with human lung fibroblasts (G. Michalopoulos, F. Russell, and C. Biles, In Vitro, 15, 796, 1979) or with mouse embryo C3H/10T1/2 cells (R. Langenbach. L. Malick, A. Tompa, C. Kuszynski, H. Freed, and E. Huberman, Cancer Res., 39, 3509, 1979) does not result in a significant long-term survival or maintenance of hepatic characteristics. Although hepatocytes cocultured with viable liver epithelial cells (C. Guguen-Guillouzo, B. Clement, G. Baffet, C. Beaumont, E. Morel Chany, D. Glaise, and A. Guillouzo, Exp. Cell Res., 143, 47, 1983) survive for long periods and produce albumin, their capacity for chemical hepatotoxicity testing has not been determined.

Since interaction of hepatocyte precursor cells with mesenchyme or mesenchyme products seems essential for liver development in chicken (N. Le Douarin, Developmental Biology, 17, 101, 1968), we used 3T3 fibroblats, a mesenchyme derived cells, to support the long-term survival and the expression of differentiated functions of adult rat hepatocytes in culture.

DESCRIPTION OF THE INVENTION

It is now discovered that rat hepatocytes can be cultured in Vitro for long-term surviving periods under controlled conditions. These conditions allow the expression of normal hepatocyte morphology and function. The long-term in Vitro cultivation of hepatocytes is essential for several types of studies, mainly those involved in the assesment of acute, or chronic hepatotoxicity at low does of differente agents, like drugs, chemical compounds, environmental pollutants, etc.

Rat hepatocytes, or other hepatocytes, are cultivated in the presence of 3T3-fibroblasts; these cells should be treated with drugs or with ionizing radiation such as x or gamma rays to prevent their multiplication and they are necessary for maintaining normal morphology and expression of hepatocyte function for long-term periods. Hepatocytes can also be cultivated without 3T3 layer with medium containing fibroblast derived products, but a suitable treatment of the surface of culture vessels should be made.

Fibroblasts or fibroblast cell products are essential to support long-term cultivation of hepatocytes. However, the presence of fibroblast cell products is not sufficient, since a modification of the substrate on which liver cells are going to attach should be made. The substrate modification is overcome if 3T3-fibroblasts are used as cell layers. Treated 3T3-cells, besides supporting a normal expression of hepatocyte function in long-term periods, they also contribute to growth inhibition of viable fibroblasts present in the liver if other hormones are added to the culture medium.

Suitable fibroblastic cells may include others than 3T3 mouse fibroblasts. However, 3T3 were chosen because they are a well characterized cell line easier to use than other cells in culture, and because they are suitable for cultivation of other diploid epithelial cells, as it was shown for the serial growth of keratinocytes (J. G. Rheinwald and H. Green, Cell, 6, 317 and 6, 331; 1975).

3T3-cells are treated with mitomycin-C, an agent that damage DNA, or with inonizing radiation such as x or gamma rays, until the cells ability to produce progeny is destroyed, and the treatment is carried out before cells are inoculated or irradiated into the culture vessels preventing their multiplication and the overgrowth of hepatocytes.

Fibroblast cell density should be high enough, so the hepatocytes can attach on top expressing their normal morphology and functions. Conveniently, fibroblast cells are inoculated at a density from about 30,000 to about 65,000 cells/cm$^2$ and said hepatocytes at a density from about 180 to about 35,000 cells/cm$^2$.

Several cell culture medium might be suitable for cultivating hepatocytes as described herein. Culture media are synthetic formulations containing glucose, salts, aminoacids, vitamins, growth factors, etc. We used one of these commercially available cell culture medium, i.e. the Dulbecco-Vogt modification of Eagle's medium supplemented with 10% calf serum, also fetal calf serum could be used. Furthermore, it may contain modifiers of mixed-function oxidases such as $2 \times 10^{-3}M$ phenobarbital, 3-methycholanthrene, Aroclor 1254 or SKF525-A, as well as the medium conditioned by the fibroblast cells.

The hepatocyte nature of the cultivated cells was substantiated by several parameters: polygonal and typical morphology of parenchymal liver cells, expression of cytochrome P-450 and its inducibility by phenobarbital, response of the cultured cells to hepatotoxic drugs, and electron micropraphs of sections through the cultured cells confirming their typical ultrasturcture of hepatocytes.

In these long-term culture conditions, besides hepatocytes, other cell types from liver (endothelial cells, Ito cells, Kupffer cells) can be also cultivated with some modifications of this procedure.

It has been found that some hormones should be added to the culture medium; insulin at 5 $\mu$g/ml, hydrocortisone at an optimal of 25 $\mu$g/ml (a rather high concentration as compared to other epithelial cells), but concentrations ranging from 1-100 $\mu$g/ml can be used; a low concentration of hydrocortisone (1-5 $\mu$g/ml) allow the growth and differentiation of Ito cells. Hydrocortisone, and the 3T3-fibroblast layer are needed for both the expression of hepatocyte normal morphology and function, and the inhibition of liver fibroblast overgrowth.

Using the process described herein, rat hepatocytes and hepatocytes from other species such as humans, mammals, birds, reptiles, amphibians and fishes can be cultivated in long-term survival conditions for differentiation, gene expression, metabolic and toxicological studies.

These cultures provide a suitable biological system for studying hepatocyte normal and pathological functions, and for hepatoxicity testing of drugs, chemical compounds and environmental pollutants, and very importantly, for screening drugs with the ability to exert modifications in liver function. The Federal Register of the United States reported that in 1978, more than 70,000 chemical compounds were under commercial production and among 700 to 3,000 new chemicals are being introduced per year (Federal Register, U.S.A. 43, 50140, 1978). From these only 6,000 have been studied as possible toxic agents (L. Fishbein, Studies in Environmental Sciences, 4, 2, 1979). Therefore more than 60,000 remain unknown regarding their potential risk for humans. Many of the new chemicals that are made should be tested in systems in Vitro before they are tested in animals to help predict their usefulness and toxicity. On the other hand, this procedure might be also suitable for the cultivation of hepatocytes from primates and humans for the aforementioned purposes, and for its important application in vaccine production against viruses that can cause pathological alterations in liver, like hepatitis, on other biological agents like plasmodium, entamoeba, etc.

And last but not least, these cultures produce intermediate metabolites with biological and toxicological action on other organ cells for assessment.

SUMMARY OF THE INVENTION

It is therefore a main object of the present invention to provide a long-term surviving culture of hepatocytes permitting them to maintain their morphological and functional characteristics for long-term periods.

It is still a main object of the present invention to cultivate hepatocytes under long-term surviving conditions for differentiation, gene expression, metabolic and toxicological assessment.

It is another main object of the present invention to provide a process for the long-term surviving culture of hepatocytes in order to maintain said hepatocytes alive for long-term periods keeping their morphological and functional characteristics.

It is further main object of the present invention to provide a method for the assessment of acute and chronic hepatotoxicity of drugs, chemicals, biologicals and environmental pollutants, by treating the long-term surviving culture of hepatocytes with said hepatotoxic agents.

Still another object of the present invention to provide a method for the preparation of a vaccine against the hepatitis by treating the long-term surviving culture of hepatocytes with virus of hepatitis and either separating the protein produced therein to prepare the vaccine or separating the multiplied viruses and inactivating them to prepare the vaccine.

These and other objects of the invention may be apparent to the skilled in the art from the above description of the invention and from the following examples.

EXAMPLE 1

Obtention of hepatocyte suspension for in Vitro cultivation.

Liver was perfused in situ with salt solution via the portal vein, at 37° C. and 15 ml/min. for 3 min. Perfusion was repeated with 100 units/ml of collagenase in salt solution at 37° C. and at 10 ml/min. Cells were dispersed by gently shaking the exised liver in 40 ml of Dulbecco-Vogt modified Eagle's culture medium, supplemented with 10% calf serum, 5 $\mu$g/ml insulin and $10^{-7}M$ d-biotin. Cell suspension was filtered through a nylon mesh of 200 $\mu$m and allowed to stand for 10 min. Supernatant was discarded and cells were resuspended in 12 ml of supplemented culture medium. Hepatocytes were inoculated at 35,000/cm$^2$ in culture dishes containing 3T3 cells treated with mytomicin-C, and placed in a 37° C. humidified incubator gassed with 90% air-10% $CO_2$. After 1 h, non-attached hepatocytes were discarded, cultures were rinsed with serum-free medium; and refed with medium supplemented as before plus 25 $\mu$g/ml hydrocortisone. Culture medium was changed every other day.

EXAMPLE 2

Use of drug-treated 3T3-cells to support the long-term cultivation of hepatocytes.

Confluent cultures of 3T3 cells grown with Eagle's medium modified by Vogt-Dulbecco and supplemented with 10% calf serum were treated with 4 or 10 µg/ml of mitomycin-C for 2 hours at 37° C. After this incubation, cells were washed twice with isotonic salt solution, then they were trypsinized and inoculated at 30,000 cells/cm$^2$. After 24 hrs. of inoculation, hepatocytes were seeded at 35,000 cells/cm$^2$ on top of the treated 3T3 cell layer. Hepatocytes adhered to 3T3 cells and spread. Spreading took place in the first 24 hours after seeding, and liver cells began to form the characteristic hepatocyte cords in culture, with regular intercellular space resembling bile cannaliculi. Hepatocytes survived in these culture conditions for up to 2 months. Longer periods of cultivation were not carried out because they were not considered necessary for the purposes of this invention.

EXAMPLE 3

Adhesion of hepatocytes to the culture substrate.

Adhesion of hepatocytes to the culture substrate was about 80-90% and it was the same at several inoculation densities, ranging from 180 cells/cm$^2$ to 18,000 cells/cm$^2$. Confluent monolayers of hepatocytes are obtained with an inoculation density of 35,000 cells/cm$^2$. The same proportion of adhered cells was observed in cultures of hepatocytes from hepatectomized (regenerating liver) and from non-hepatectomized (non-regenerating liver) rats.

EXAMPLE 4

Morphological characteristics of hepatocytes.

Figure 1B:
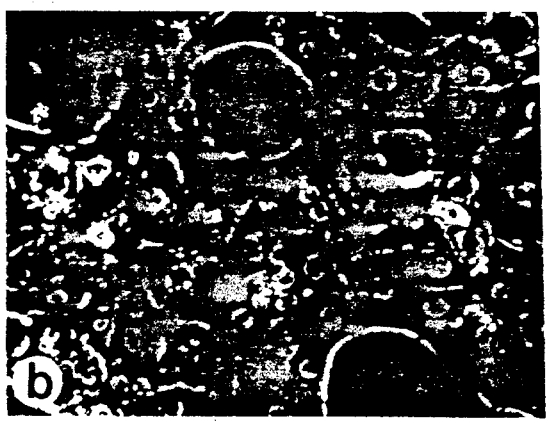

Morphology of hepatocytes cultured in long-term survival conditions (LTSC) as described in this invention appeared to be conserved for up to two months in culture; they showed their polygonal characteristic cell shape and they formed confluent groups of cells with refringent intercellular spaces (FIG. 1b, c); these spaces might be related to bile cannaliculi (C. Guguen-Guillouzo, B. Clement, G. Baffet, C. Beaumont, E. Morel-Chany, D. Glaise, and A. Guillouzo, Exp. Cell Res., 143, 47, 1983). However, hepatocytes cultured without drug-treated 3T3 fibroblasts, (standard culture conditions) lost their morphological characteristics and died in less than six days in cluture (FIG. 1a).

EXAMPLE 5

DNA synthesis in cultured hepatocytes.

Figure 2A:
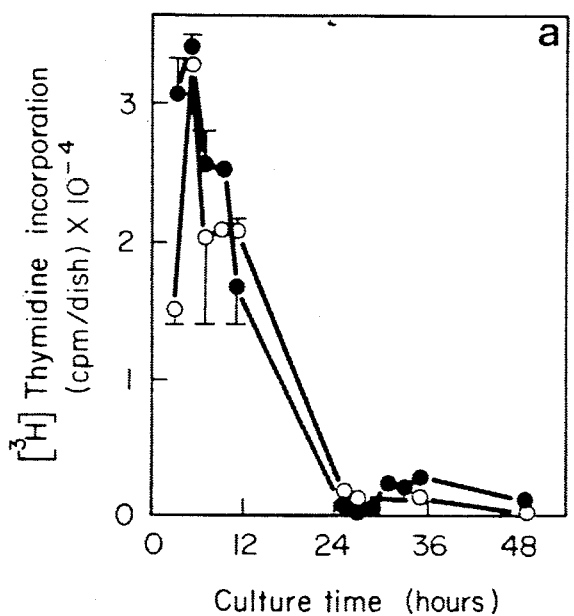
Figure 2B:
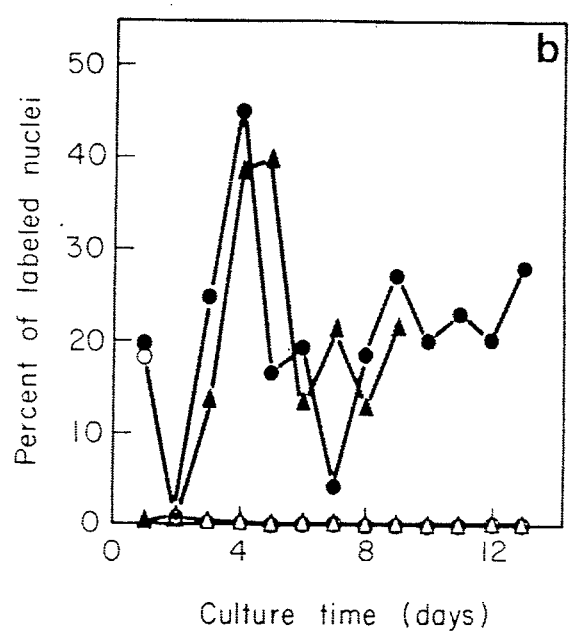
Figure 2C:
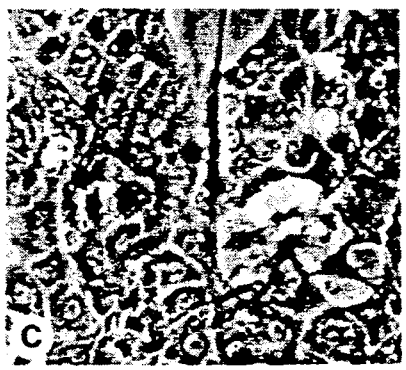
Figure 2D:
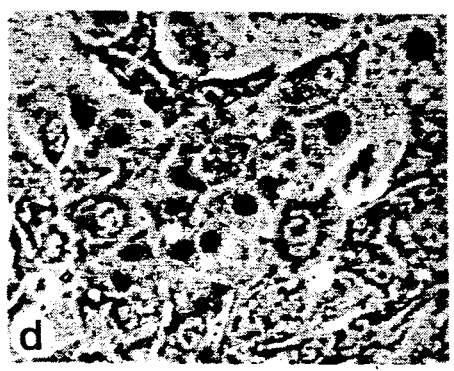

When hepatocytes cultured under standard culture conditions (SCC) and under LTSC were compared for their ability to synthesize DNA, it was observed that in both culture conditions, hepatocytes from regenerating livers showed the same rate of $^3$H-thymidine incorporation during the first 48 hrs. of culture (FIG. 2a). After this time, DNA synthesis decreased to undetectable levels in hepatocytes cultured under SCC (FIG. 2b), but hepatocytes on LTSC remained synthesizing DNA as shown by the experiments of $^3$H-thymidine labelled nuclei (FIG. 2b); DNA synthesis was also observed in hepatocytes from non-regenerating liver cultured under LTSC (FIG. 2b) but it was absent under SCC (FIG. 2b). In FIG. 2c, d we are showing that labelled nuclei in both hepatectomized and non-hepatectomized rats, correspond to cells with characteristic hepatocyte morphology.

EXAMPLE 6

Cytochrome P-450 content of cultured hepatocytes.

Figure 3B:
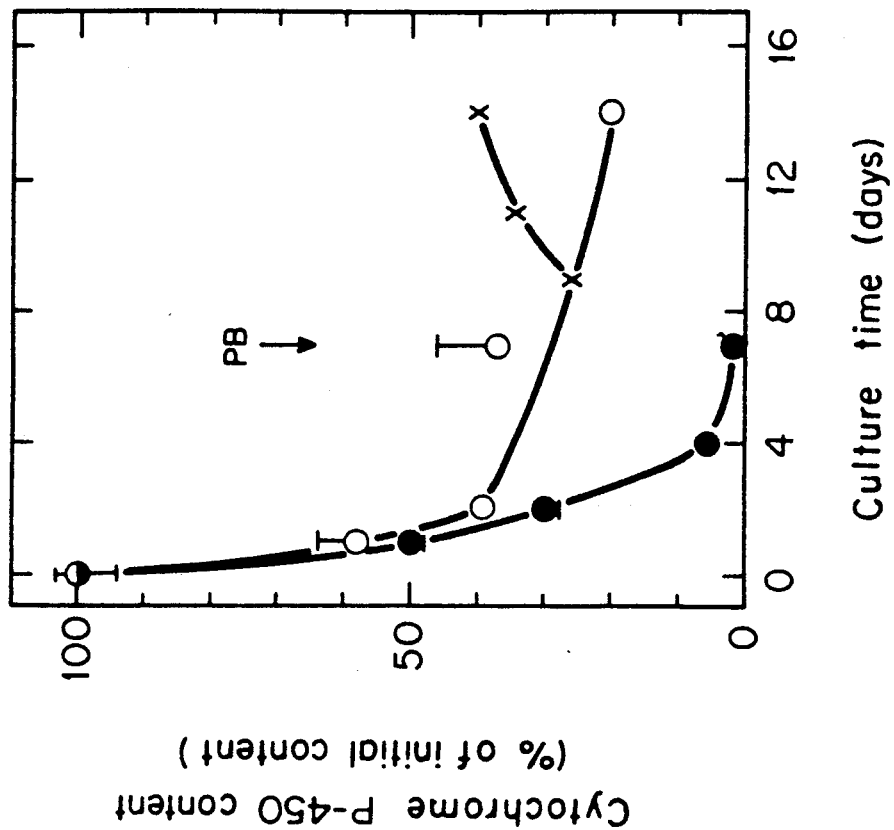
Figure 3A:
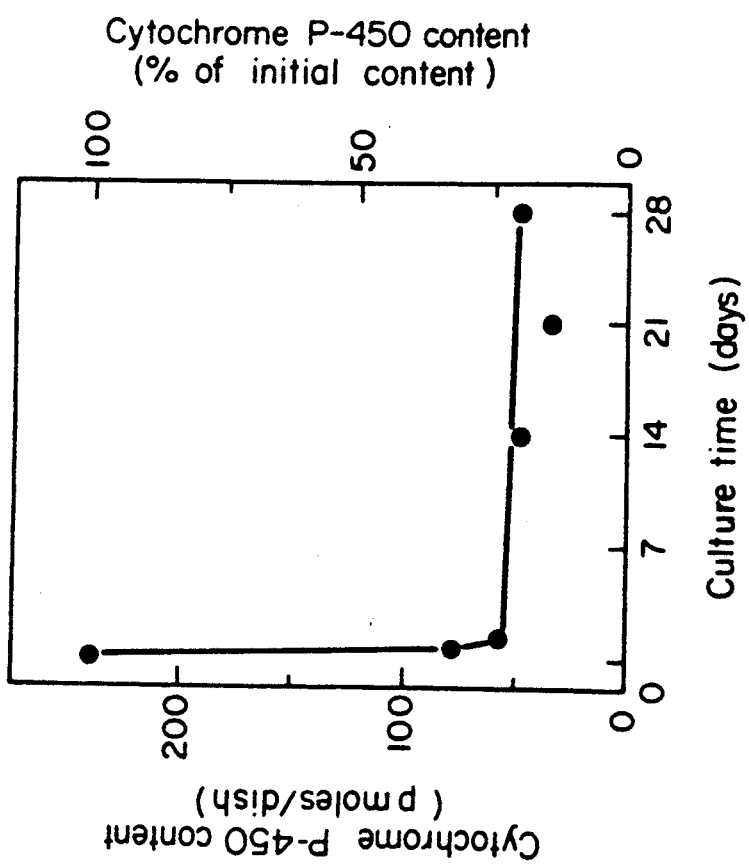

It is well known that cytochrome P-450 (cyt-P450) content decreases abruptly in hepatocytes from liver cells cultured under SCC; this decrease reaches undetectable levels after 4 days in culture (FIG. 3b). However, in hepatocytes cultured in LTSC, cyt-P450 content decreased to about 20% the initial content, and it remained constant thereafter up to 4 weeks (FIG. 3a); cyt-P450 content was not determined at longer culture times. On the other hand, the addition of $2 \times 10^{-3}$M phenobarbital to hepatocytes cultivated under LTSC exerted an induction of cyt-P450 activity increasing its content up to 2 fold (FIG. 3b). The inducibility of cyt-P450 by phenobarbital is similar to the induction observed in normal liver in vivo (A. H. Conney, Pharmacological Reviews, 19, 317, 1967).

EXAMPLE 7

Effect of hepatotoxic drugs.

An important use of hepatocytes cultivated in vitro is to asses the toxicity of drugs, chemical compounds and environmental pollutants. The assesment should be done in long-term cultures in order to test drugs at sufficiently low concentrations comparable to pharmacological doses. Therefore, the capacity of cultivated hepatocytes to respond to several hepatotoxic drugs was tested under LTSC. We selected four hepatotoxic drugs: dexamethasone, acetaminophen, aminopyrin and ethanol. Fifteen days treatment with various concentrations of dexamethasone (1-50 µg/ml) produced morphological changes and wide intercellular spaces, and hepatocytes accumulated a great amount of intracytoplasmic lipid droplets (FIG. 4b, e), resembling a fatty liver state. The addition of 100 µg/ml of acetaminophen exerted some morphological changes with conspicuous cell vacuolation, increased cytoplasmic density and bigger intercellular spaces (FIG. 4c); this effect was also observed at lower concentration of the drug, as low as 0.1 µg/ml. Treatment with aminopyrin (0.1-100 µg/ml) produced some changes in morphology; hepatocytes lost their polygonal characteristic shape and they accumulated some lipid droplets (FIG. 4d); lipid accumulation was less than in dexamethasone treated cells. Low concentrations of ethanol (0.02-1%) in the culture medium also produced some intracytoplasmic lipid accumulation (FIG. 4c). Control cultures non-treated with these drugs did not show any of the changes described (FIG. 4a). Since hepatocytes cultured under LTSC can respond to these hepatotoxic compounds showing several types of cell injury including intracytoplasmic lipid accumulation, it seems that they are adequate for toxicity testing and for studying the metabolic pathways which may lead to liver cell damage; they provide a sensitive, fast and inexpensive method, compared with in vivo animal models.

FIGURE DESCRIPTION

Figure 1C:
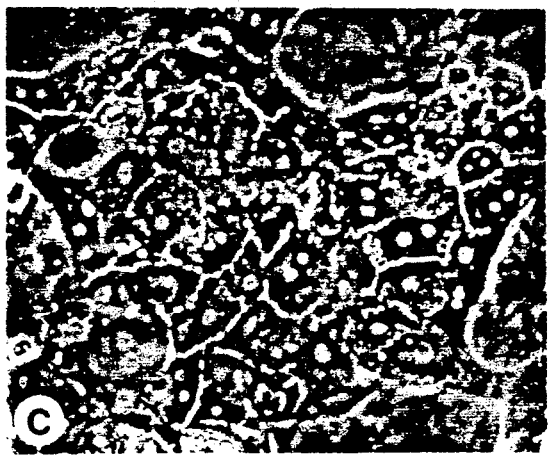

FIG. 1. Morphological characteristics of rat hepatocytes under different culture conditions. Hepatocytes were isolated from non-regenerating liver and they were inoculated into 35-mm tissue culture dishes at $3 \times 10^5$ cells/dish. At the indicated times, cells were photographed under phase contrast microscopy.

(a). Hepatocytes cultured under SCC for 6 days; (b) and under LTSC for 6 days, and (c) for 2 months. Note that normal hepatocyte morphology has dissapeared by 6 days under SCC.

FIG. 2. $^3$H-TdR incorporation into DNA of rat hepatocytes cultured under different conditions. Hepatocytes were isolated from regenerating and non-regenerating livers and they were inoculated into 35-mm tissue culture dishes at $3 \times 10^5$ cells/dish. At the indicated times, (a) cells were disrupted with 2% SDS, and macromolecules were TCA precipitated for counting of $^3$H-TdR incorporation into DNA; or (b-d) cells were fixed and processed for autoradiography and nuclear counting. (a) Cells from regenerating liver were cultured under (○) SCC or (•) LTSC; (b) labelled nuclear counting in cells cultured from regenerating liver under (○) SCC or (•) LTSC, and cells cultured from non-regenerating liver under (△) SCC and (▲) LTSC; (c) and (d) shows cultured hepatocytes with labelled nuclei from regenerating and non-regenerating livers, respectively.

FIG. 3. Cytochrome P-450 content of hepatocytes cultured under different conditions. Hepatocytes from non-regenerating livers were isolated and they were inoculated into 100-mm tissue culture dishes at $3 \times 10^6$ cells/dish. At the indicated times, cells were extracted and cytochrome P-450 content was determined spectrophotometrically in the cell extracts. (a) Cells cultured under LTSC; (b) shows phenobarbital inducibility of cyt-P450; (○) cyt-P450 in hepatocytes cultured under LTSC, (x) cyt-P450 content after induction with phenobarbital and cultured under LTSC, and (○) cyt-P450 content in hepatocytes cultured under SCC. Arrow, addition of $2 \times 10^{-3}$M phenobarbital.

FIG. 4. Effect of hepatotoxic drugs upon rat hepatocytes cultured under long-term conditions. Hepatocytes were isolated from non-regenerating rat liver and they were inoculated into 35-mm tissue culture dishes at $3 \times 10^5$ cells/dish; cells were cultured under long-term conditions and drugs were added after 24 hrs. or inoculation. Cells were photographed at 15 days of culture under phase contrast microscopy. (a) Controls, hepatocytes non-treated with drugs; (b) cultures treated with dexamethasone fosfate 50 µg/ml; (c) acetaminophen, 100 µg/ml, (d) aminopyrine, 100 µg/ml. In (e) lipid accumulation in hepatocytes after 30 days treatment with different concentrations of (•) dexamethasone fosfate solution in bi-distilled H$_2$O, (○) dexamethasone in ethanol, and (△) ethanol. Arrowheads, cells with lipid accumulation; arrows, vacuolation of cells; double arrows, increased intercellular spaces.

What is claimed is:

1. A method for the assessment of toxicological, chemical, biological and pharmacological agents, comprising: treating long-term surviving cultured hepatocytes with said agents at diverse concentrations, said long-term surviving cultured hepatocytes comprising hepatocyte cells at a density of from about 180 to about 65,000 cells/cm$^2$ in a culture medium containing from about 1 to about 100 µg/ml of hydrocortisone, in the presence of either multiplication inhibited fibroblast cells or fibroblast cell products on a modified substrate, at controlled densities of from about 30,000 to about 65,000 cells/cm$^2$, assessing said hepatocyte cells for injury caused by said agents.

2. The method as claimed in claim 1, wherein the treatment of said hepatocytes with said agents produce intermediate metabolites with biological and toxicological action on other organ cells.

* * * * *